United States Patent [19]
Oh et al.

[11] Patent Number: 5,689,059
[45] Date of Patent: Nov. 18, 1997

[54] SELECTIVE GAS SENSOR

[75] Inventors: Seajin Oh; Jose Joseph, both of Palo Alto, Calif.; Neil Adams, Novi, Mich.; Daniel A. Young, Gurnee; Gary K. Mui, Wheeling, both of Ill.

[73] Assignee: Motorola, Inc., Schaumburg, Ill.

[21] Appl. No.: 696,550

[22] Filed: Aug. 14, 1996

[51] Int. Cl.⁶ .................................................. G01N 7/00
[52] U.S. Cl. ...................... 73/23.31; 73/31.05; 204/408
[58] Field of Search ............................ 73/23.31, 23.32, 73/31.05; 60/276; 204/408

[56] References Cited

U.S. PATENT DOCUMENTS

| | | |
|---|---|---|
| 3,607,084 | 9/1971 | Mackey et al. . |
| 3,906,721 | 9/1975 | Micheli et al. . |
| 4,033,169 | 7/1977 | Fujishiro et al. . |
| 4,244,918 | 1/1981 | Yasuda et al. . |
| 4,329,873 | 5/1982 | Maeda . |
| 4,329,874 | 5/1982 | Maeda . |
| 4,927,517 | 5/1990 | Mizutani et al. . |
| 5,250,169 | 10/1993 | Logothetis et al. . |
| 5,296,196 | 3/1994 | Takeshima . |
| 5,476,001 | 12/1995 | Hoetzel et al. . |
| 5,505,073 | 4/1996 | Gerblinger et al. . |
| 5,505,837 | 4/1996 | Friese et al. ............................ 204/425 |

FOREIGN PATENT DOCUMENTS 0 259 175   3/1988   European Pat. Off. .

OTHER PUBLICATIONS

"A Novel Catalytic Sensor for Monitoring the Concentration of Mixed Combustible Gases," Luo, Rui–Xian et al. Science in China (Series A) Dec., 1991; vol. 34, No. 12 pp. 1500–1507.
"A Low Power Integrated Catalytic Gas Sensor," P. Krebs and A. Grisel Sensors and Actuators B, 13–14 1993 pp. 155–158.
"Chemical and Physical Sensors Based on Oxygen Pumping With Solid–State Electrochemical Cells," E.M. Logothetis, et al. Sensors and Actuators B. 9 (1992) pp. 183–189.
"Sensors for Measuring Combustibles in the Absence of Oxygen," J.H. Visser, et al. Sensors and Actuators B. 9 (1992) pp.m 233–239.

Primary Examiner—Michael Brock
Assistant Examiner—Jay L. Politzer
Attorney, Agent, or Firm—Jasper W. Dockrey

[57] ABSTRACT

A selective gas sensor (10) for detecting a particular compound, or group of compounds, such as non-methane hydrocarbons, within a high temperature gas stream (12) includes an oxygen generation system (14) positioned over an oxygen diffusion region (15). The oxygen generation system (14) and the oxygen diffusion region (15) provide oxygen through a medial temperature control zone (20) to a sensing element (16). The temperature and flux of hydrocarbon components within the high temperature gas stream (12) are regulated by components within the high temperature control zone (20) and by an external temperature control zone (22) in thermal contact with the sensing element (16).

17 Claims, 3 Drawing Sheets

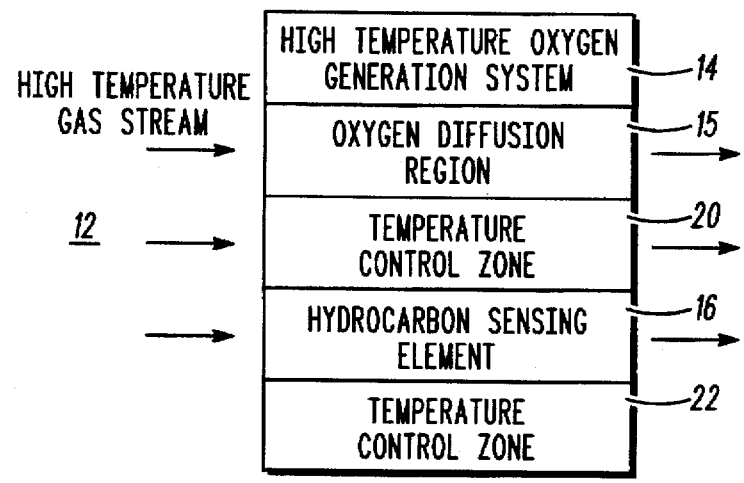
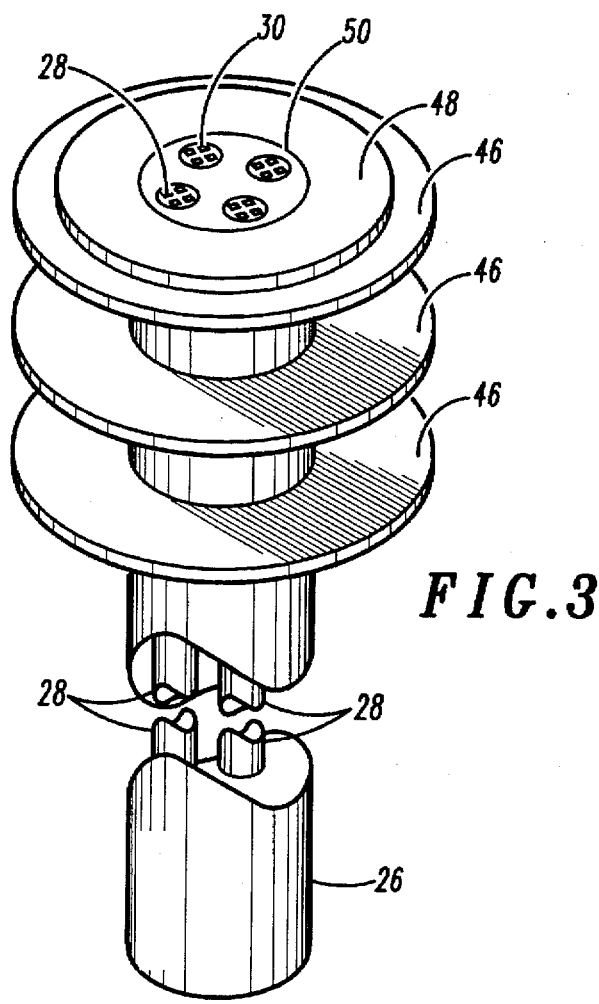

SELECTIVE GAS SENSOR

FIELD OF THE INVENTION

This invention relates, in general, to gas component sensors, and more particularly, to gas sensors containing a sensing element showing temperature dependent selectivity for various components of a high temperature gas stream.

BACKGROUND OF THE INVENTION

Sensors for the detection of particular compounds present in a high temperature gas stream find numerous applications in many different mechanical systems. For example, detection of certain compounds in a high temperature gas stream is important in industrial emission monitoring for detection of gas pollutants, such as sulfur dioxide ($SO_2$), in residential heating systems for detection of carbon monoxide (CO), and in automobile exhaust systems for various compounds including hydrocarbons.

In automotive applications, gas sensors can be placed at various locations in an exhaust system. Exhaust gas from an internal combustion engine typically contains hydrogen ($H_2$), carbon monoxide (CO), methane ($CH_4$), carbon dioxide ($CO_2$), nitric oxide (NO), water ($H_2O$), and non-methane hydrocarbons ($C_nH_m$), where n is an integer larger than 1 and m is an integer whose value depends upon the kind of hydrocarbon compound, for example, alkane, alkene, alkyl, or aryl. Important environmental pollution concerns dictate that the emission of hydrocarbons be minimized. To minimize pollutants in the engine exhaust, sensors can be placed before and after the catalytic converter to monitor the performance of the converter. Also, the emission of hydrocarbons can be controlled, in part, by an engine exhaust control system that receives a feedback signal from an exhaust sensor capable of selectively detecting the presence of hydrocarbons in the engine exhaust.

For proper operation, a gas sensor must be built to operate within the high temperature and corrosive environment of a gas stream emerging from one of the mechanical systems described above. In addition, the sensor must contain a sensing element capable of selectively detecting the presence of a particular compound. For example, in the automotive application, it is desirable to detect the presence of hydrocarbons having a molecular weight greater than methane. Several types of sensing elements have been developed for detecting various chemical species within a gas stream. Existing gas sensing elements include calorimetric sensors having a catalyst coating, semiconductor metal oxide based sensors, mixed-potential electrochemical sensors, or amperometric electrochemical sensors.

In the case of automotive exhaust sensors, the gas sensing elements disclosed in the prior art typically exhibit higher selectivity to detection of non-methane hydrocarbons within specific temperature ranges. Although the sensing element performs best in a specific temperature range, the temperature of the gas stream into which the sensor is submerged often varies over time. For example, automobile engine operation is dynamic and the exhaust gas temperature varies from ambient temperature at engine start-up to more than 1000° C. during periods of high power operation. In addition to engine operating conditions, the temperature of the exhaust gas within the exhaust system changes with distance from the engine. Typically, the temperature range of maximum non-methane hydrocarbon sensitivity is below the temperature of the automobile exhaust gas stream during normal engine operation after warm-up, yet above ambient temperatures.

In addition to the thermal variations associated with gas dynamics, some types of sensing elements experience thermal loading from additional, heat-generating components required for their operation. For example, calorimetric sensors require an oxygen source for the catalytic oxidation of the hydrocarbons on a sensitive region of the sensing element. Typically, oxygen supply systems used in catalytic gas sensors operate at a temperature that exceeds the temperature range of maximum hydrocarbon selectivity for the sensor. Most often, the best performance of the sensing element is obtained at a temperature that is below both the operating temperature of the electrochemical oxygen pump and the steady-state temperature of the exhaust gas stream.

Efficient operation of a selective gas sensor requires that the sensor housing be designed to maintain the sensing element at its optimum operating temperature. Accordingly, a need existed for an improved sensor design that maintains optimum operating efficiency of a selective sensing element.

BRIEF DESCRIPTION OF THE DRAWINGS

FIG. 1 is a schematic block diagram of a selective gas sensor having independent temperature control zones arranged in accordance with the invention;

FIG. 3 is an inverted perspective view of a heat pipe assembled in accordance with one embodiment of the invention.

Figure 2:
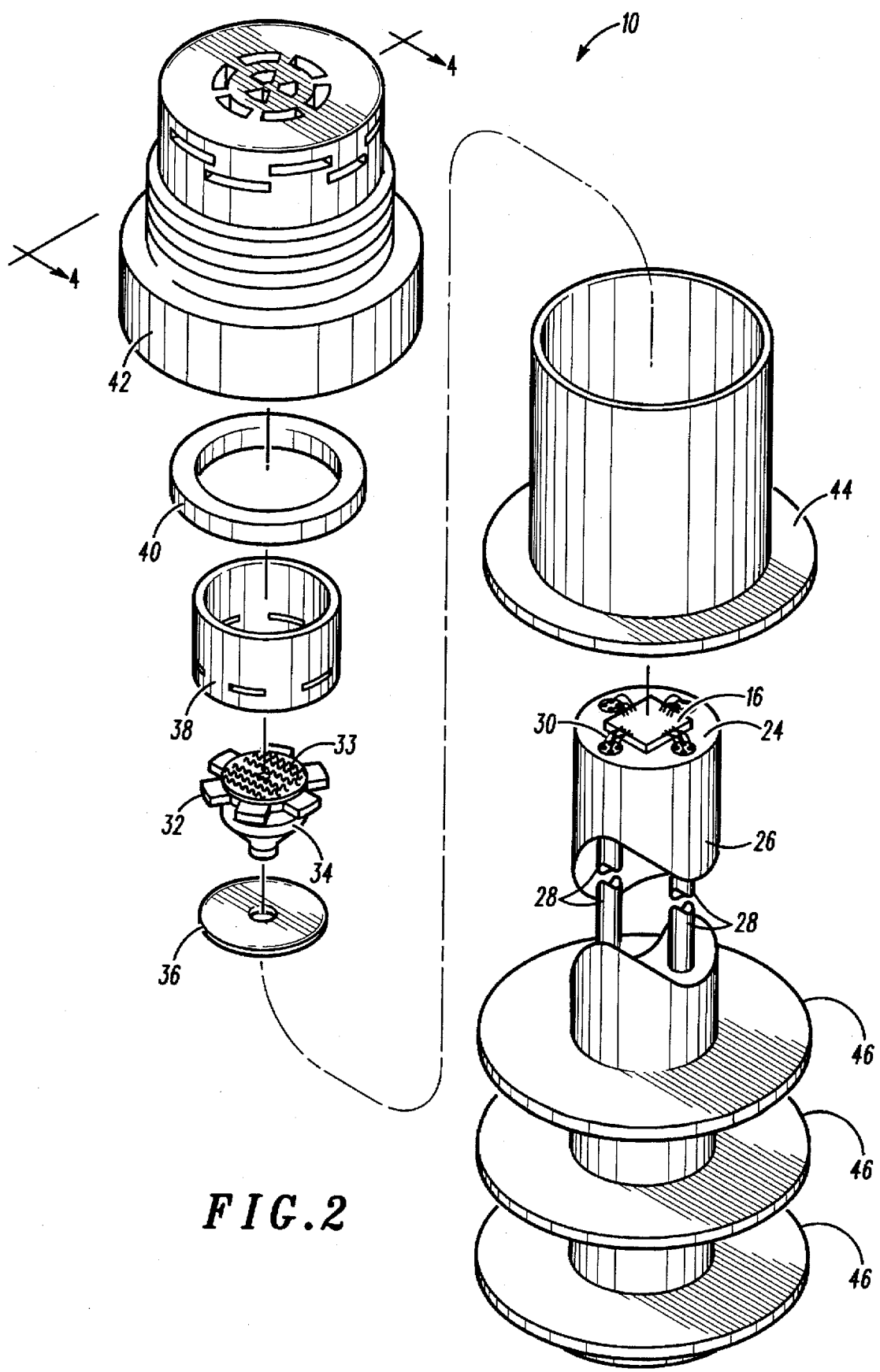
FIG. 2 is an exploded assembly view of a selective gas sensor arranged in accordance with one embodiment of the invention.

It will be appreciated that for simplicity and clarity of illustration, elements shown in the FIGURES have not necessarily been drawn to scale. For example, the dimensions of some of the elements are exaggerated relative to each other. Further, where considered appropriate, reference numerals have been repeated among the FIGURES to indicate corresponding elements.

DETAILED DESCRIPTION OF PREFERRED EMBODIMENTS

The present invention is for a selective gas sensor capable of detecting the presence of a particular component in a high temperature gas stream. The selective gas sensor is configured to maintain separate regions of the sensor at different temperatures, and to maintain temperature gradients within the sensor. In one embodiment of the invention, a calorimetric sensing element is employed to determine the presence of non-methane hydrocarbons by sensing the heat given off when hydrocarbons are oxidized on the sensor. Previous sensor designs have not addressed the need to maintain an optimum hydrocarbon gas flow to the sensing element, nor have prior art sensors addressed the need to thermally stabilize the internal environment of the sensing element and control the hydrocarbon gas temperature impinging on the sensor. The selective gas sensor described herein effectively accommodates the conflicting operating temperatures of the oxygen pump and the sensing element, while both are immersed in a high temperature gas stream. In addition to hydrocarbon detection, the selective gas sensor of the invention can be employed in other applications, such as the detection of CO in a building heating system, $SO_2$ emissions from a coal fired power plant, and the like.

Shown in FIG. 1 is a schematic block diagram illustrating the regions of thermal management within a selective gas sensor 10 of the invention. The sensor is immersed in a high temperature gas stream 12. In one important application of the invention, gas stream 12 is an engine exhaust emerging from an internal combustion engine. Gas stream 12 passes through selective sensor 10 at a temperature typically ranging from ambient air temperature at engine start to 1150° C. at high power output. In steady-state operation, the exhaust temperature is usually between 500° C. and 800° C. Under steady-state conditions, the gas sensor temperature would eventually become equal to the temperature of the gas stream, or some other temperature between that of the gas stream and the oxygen pump.

To counter gas temperature variations and to avoid arriving at thermal equilibrium with high temperature gas stream 12, selective gas sensor 10 employs at least five distinct thermal management zones. A high temperature oxygen generation system 14 is separated from a sensing element 16 by an oxygen diffusion region 15 and a medial temperature control zone 20. Sensing element 16 is further temperature controlled by an external temperature control zone 22.

The thermal regions identified in FIG. 1 function to maintain the temperature of sensing element 16 at its most effective operating temperature. For example, at a temperature below about 400° to 600° C., sensing element 16 exhibits maximum sensing selectivity to hydrocarbons having a molecular weight exceeding that of methane. Meanwhile, the electrochemical oxygen pump used in high temperature oxygen generation system 14 most effectively operates at a temperature of about 800° C. Accordingly, the thermal management regions function to maintain a large temperature gradient while selective sensor 10 is immersed in a gas stream having an average temperature intermediate to that of the electrochemical oxygen pump and the hydrocarbon sensing element.

Within the general conceptual framework of the invention, medial temperature control zone 20 primarily functions to provide sensing element 16 with a small, representative sample of the high temperature gas stream entering selective sensor 10. By limiting the quantity of gas impinging on sensing element 16, less heat is available to be transferred from the gas to the sensing element.

In cooperation with medial temperature control zone 20, external temperature control zone 22 functions to conductively cool sensing element 16. Working together, the temperature control zones provide thermal management of both the gas stream impinging upon the sensing element and the temperature of the sensing element itself. Oxygen diffusion region 15 provides both an oxygen diffusion pathway and thermal insulation between the electrochemical oxygen pump and the sensing element.

Those skilled in the art will appreciate that various housing designs and component arrangements can be defined to construct a selective gas sensor incorporating the thermal management zones of the invention. Accordingly, the following preferred embodiment describes a detailed design of one possible component arrangement of a selective gas sensor incorporating the thermal management zones illustrated in FIG. 1. However, other housing designs can incorporate the thermal management zones of the invention and they are within the scope of the invention.

FIG. 2 illustrates an assembly view of a selective sensor 10 arranged in accordance with one embodiment of the invention. A sensing element 16 is mounted on a heat transfer surface 24 of a thermally conductive heat pipe 26. Preferably, heat pipe 26 is constructed of a material having a large heat capacity to minimize and dampen temperature fluctuation of the gases in second chamber 64 and of sensing element 16. For example, heat pipe 26 can be material having a high thermal conductivity, such as copper, stainless steel, and the like. Alternatively, heat pipe 26 can be constructed of an electrically insulating material, such as alumina. In addition to temperature variation dampening, in the present embodiment, heat pipe 26 encloses a plurality of ceramic rods 28 that provide conduits for electrical wires 30.

Sensing element 16 is a silicon micromachined sensor having sensing components integrated together on a silicon chip. Sensing element 16 is preferably a calorimetric catalytic sensor. This type of catalytic gas sensor typically employs a differential calorimeter. Each individual member includes a heater element and a thermometer element overlying a thin-film area. The thin-film area is formed by depositing a layer of silicon dioxide or silicon nitride on a silicon substrate, then etching away a portion of the silicon substrate to expose the underside of the deposited thin-film. A catalyst material, such as platinum (Pt), palladium (Pd), gold (Au), and the like, is deposited onto the temperature measurement element to catalyze an oxidation reaction. When a selected gas is oxidized on the catalyst, the exothermic heat of the oxidation reaction is measured by the change in the electrical resistance of the temperature measuring element.

Many different arrangements for the sensor components are known in the art and are contemplated for use in the present invention. One such silicon-based catalytic gas sensor, for example, is described in "A Low Power Integrated Catalytic Gas Sensor," P. Krebs, et al., Sensors and Accuators B, Vol. 13–14 (1993), pp. 155–158. A ceramic-based catalytic gas sensor, for example, is described in "A Novel Catalytic Sensor for Monitoring The Concentration Of Mixed Combustible Gases," R. Luo, et al., Science In China (Series A), Vol. 34, 12, (1991), pp. 1500–1507. Catalytic gas sensors are also disclosed in U.S. Pat. No. 5,505,837 to Friese, et al. and U.S. Pat. No. 5,250,169 to Logothetis, et al. Alternatively, sensing element 16 can be a Taguchi-type gas sensor employing a metal oxide, such as tin oxide ($SnO_2$). A semiconductor metal oxide base sensor is disclosed in, for example, U.S. Pat. No. 4,033,169.

An electrochemical oxygen pump 32 and pump housing 34 are positioned over a gas-permeable membrane 36. A mechanical support frame 38 encloses electrochemical oxygen pump 32, pump housing 34, and gas permeable membrane 36. A thermal insulator ring 40 fits over mechanical support frame 38 and provides thermal insulation between mechanical support frame 38 and a threaded metal housing 42. Threaded metal housing 42 couples with a support tube 44 to enclose the sensor elements and to strengthen the housing assembly. Preferably, support tube 44 is constructed a material having low thermal conductance, such as from stainless steel, in order to suppress heat flow from threaded metal housing 42 into heat pipe 26.

To provide maximum heat transfer surface area, heat pipe 26 can be optionally fitted with a plurality of disks 46. Disks 46 are orthogonally connected to heat pipe 26 and are thermally coupled to the heat pipe such that an expanded heat transfer surface is provided.

An inverted perspective view of heat pipe 26 and related components is shown in FIG. 3. A bottom plate 48 is attached to the most distal heat transfer disk and surrounds the bottom surface 50 of heat pipe 26. The terminal ends of electrical wires 30, carried by ceramic rods 28, are exposed at bottom surface 50. Electrical wires 30 can be coupled to external electronic circuitry (not shown) by making electrical connections at bottom surface 50.

Those skilled in the art will appreciate that many different types of thermally conductive bodies can be utilized to perform a heat transfer function. Although the detailed illustration shown in FIGS. 2 and 3 provides a description of one embodiment of a thermally conductive body, other designs can be utilized to provide the thermal management function of temperature control zone 22. For example, heat pipe 26 can be a fully functional heat exchanger employing a heat transfer fluid mechanically pumped through the heat pipe, or an electric cooling system, or the like. Additionally, heat pipe 26 can be constructed of materials having lower thermal conductivity, such as alumina, silicate glass, and the like. Further, numerous geometric designs exist for expanding the heat transfer surface of heat pipe 26. For example, the outer wall of heat pipe 26 can be textured, or bifurcated, to expand the surface area of the heat pipe.

Figure 4:
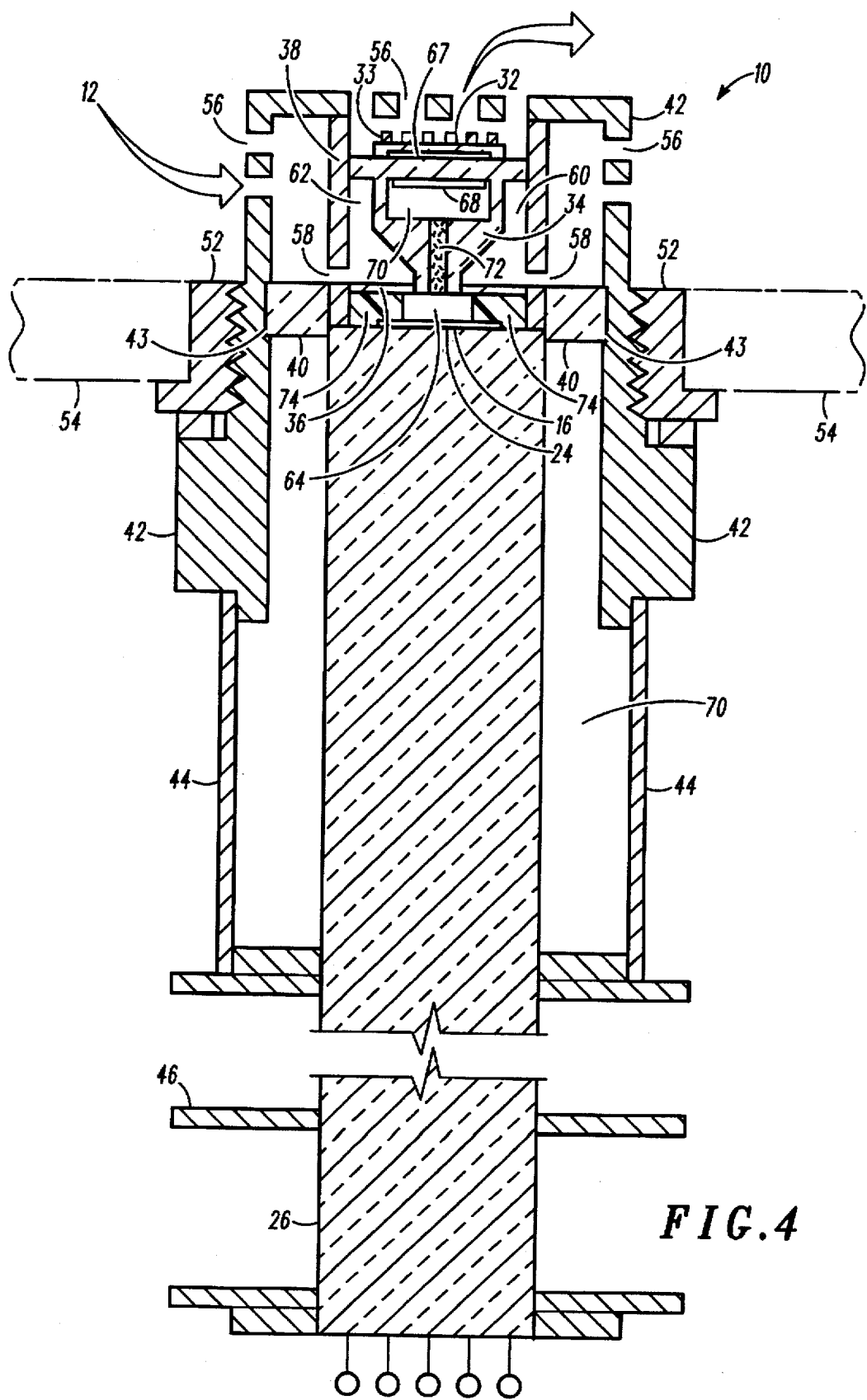
FIG. 4 is a cross-section of the selective gas sensor shown in FIG. 2 taken along section line 4—4.

A cross-sectional view of the assembly illustrated in FIG. 2 taken along section line 4—4 and mechanically attached to a metal wall is shown in FIG. 4. Threaded metal housing 42 engages a threaded boss 52 inserted into a metal wall 54. Metal housing 42 contains a plurality of gas ports 56 through which gas stream 12 can flow. Further, mechanical support frame 38 contains gas ports 58 that cooperate with gas ports 56 and oxygen pump support 34 to provide a passage for the flow of gas stream 12 past membrane 36 and oxygen pump 32.

Membrane 36 spans an interior cavity 60 within support frame 38 and divides cavity 60 into two chambers. A first chamber 62 encloses pump support 34 and oxygen pump 32, while a second chamber 64 encloses sensing element 16. As will subsequently be described in more detail membrane 36 is preferably a thermally insulating, gas-permeable member through which a selected component of gas stream 12 can diffuse. For example, membrane 36 can be a porous ceramic plate, or a ceramic sheet having perforations in the sheet allowing for the flow of gas stream 12 through the perforations. In addition to providing a thermal insulating region, membrane 36 regulates the flux of the constituents of gas stream 12 to the surface of sensing element 16. Alternatively, where selective sensor 10 is to be operated in a low temperature environment, membrane 36 can be a porous polymer material.

Oxygen pump 32 has an upper electrode 67 exposed to gas stream 12 and a lower electrode 68 facing an oxygen storage chamber 70 housed within pump support 34. A heating element 33 overlies upper electrode 67 and is separated from the upper electrode by an insulating portion of pump housing 34. Heating element 33 resistively heats oxygen pump 32 by passing electrical current through a convoluted pattern of platinum leads overlying the pump housing.

In operation, oxygen pump 32 extracts oxygen atoms by the electro-dissociation of oxygen containing compounds within gas stream 12. The oxygen obtained from the oxygen containing compounds is conducted to lower surface 68 where oxygen is released into oxygen storage chamber 70. Oxygen storage chamber 70 provides a reservoir of oxygen available to supply large amounts of oxygen to second chamber 64 for a brief period of time, while simultaneously collecting oxygen produced by the slow, steady-state operation of oxygen pump 32. A diffusion conduit 72 provides a pathway for the diffusion of oxygen from oxygen storage chamber 70 to second chamber 64.

Preferably, oxygen pump 32 is a conventional electrochemical pump including an oxygen-ion conducting solid electrolyte sandwiched between two platinum electrodes. The electrolyte is a zirconia compound, such as yttria-doped zirconium oxide (Y, $ZrO_2$). Oxygen pumped from gas stream 12 to oxygen storage chamber 70 can diffuse through diffusion conduit 72 to second chamber 64. Preferably, diffusion conduit 72 is filled with a porous material to suppress the backflow of gas components from gas stream 12. In addition to providing a diffusion conduit, pump support 34 also provides thermal insulation between the high temperature oxygen pump and the lower temperature gas within second chamber 64. Preferably, pump support 34 is a solid ceramic material resistant to the diffusion of gas species.

Oxygen diffused to second chamber 64 through conduit 72 mixes with the selected gas diffusing through membrane 36 into second chamber 64 and oxidizes the gaseous compound at the surface of sensing element 16. The corrosion of electrical wires 30, shown in FIG. 2, by the oxidative environment within second chamber 64 is prevented by covering electrical wires 30 and the bonding pads of sensing element 16 (not shown) with a protective material 74.

The operation of the embodiment illustrated in FIG. 4 in relation to the gas dynamics of gas stream 12 and the thermal management zones illustrated in FIG. 1 will now be described. The proper function of selective gas sensor 10 requires that the sensor housing be designed such that a small, representative mass of a selected gas be brought in contact with sensing element 16 at a high flow rate. Rapid movement of gas through the passages and chambers of gas sensor 10 is important to minimize response time required for changes in component concentrations within gas stream 12 to be reflected in the gas volume in the vacinity of sensing element 16. In addition, rapid gas flow is important to minimize the amount of heat transfer that occurs between the gas and the sensor components.

In addition to stringent mass transfer requirements through the gas passages and housings within sensor 10, heat conduction from high temperature components, such as electrochemical oxygen pump 32 must be minimized. The component arrangement illustrated in FIG. 4 represents one method for providing the proper mass transfer and heat transfer characteristics necessary for the highly selective detection of a selected gas, such as non-methane hydrocarbons within gas stream 12.

Referring to FIGS. 1 and 4, high temperature oxygen generation system 14 is represented by oxygen pump 32. Oxygen diffusion region 15 is represented by pump support 34. Medial temperature control zone 20 is represented by mechanical support frame 38, and by gas-permeable membrane 36. Finally, external temperature control zone 22 is represented by heat pipe 26 and thermal insulator ring 40.

The maintenance of the separate thermal control zones illustrated in FIG. 1 requires careful selection of construction materials for the various components of selective sensor 10. For example, thermal conduction of threaded metal housing 42 should be minimized, however this element must provide adequate mechanical strength to protect the internal components of selective gas sensor 10 and provide a mounting support for attachment of the gas sensor to a metal wall, such as an automobile exhaust pipe. Preferably, threaded metal housing 42 is constructed from high strength steel.

Mechanical support frame 38 must provide mechanical support and protection for the oxygen pumping and diffusion systems and protect sensing element 16 from contamination by corrosive components within gas stream 12. Preferably, mechanical support frame 38 is a ceramic element. Although support frame 38 has been illustrated with gas ports 58 for the flow of selected gas into cavity 60, mechanical support frame 38 can also be a porous ceramic material through which selected gases can diffuse into cavity 60.

Thermal insulator ring 40 must minimize the heat flow from threaded metal housing 42 and provide a gas impermeable barrier to prevent the leakage of gas stream 12 outward from metal wall 54 and along heat pipe 26. Insulator ring 40 is held in place by a circumferential groove 43 in housing 42. Preferably, thermal insulator ring 40 is a ceramic ring coated with a surface hardener.

Gas permeable membrane 36 functions as a mass transport barrier that limits the flux of selected gases entering second chamber 64 and contacting sensing element 16. In order to maintain a stable relationship between the gas flux entering second chamber 64 and the concentration of selected gas in gas stream 12, membrane 36 is fabricated to withstand high temperature and corrosive gases. Preferably, membrane 36 is constructed from porous ceramic or stainless steel frit. To further enhance the mass transfer regulating function of membrane 36, the temperature of the membrane is stabilized to minimize temperature-dependent gas diffusivity through the membrane. Temperature stability is provided by maintaining good thermal contact to heat pipe 26 through mechanical support frame 38, and by maximizing the thermal mass of the membrane. Additionally, the temperature of membrane 36 may be controlled by a heater (not shown) either embedded in or placed in proximity to the membrane.

Those skilled in the art will recognize the dynamic relationship between the mass transfer characteristics of gas permeable membrane 36, the gas volume of second chamber 64, and the sensitivity of sensing element 16. For example, the volume of second chamber 64 can be minimized or eliminated entirely when it is desirable to reduce the time required for sensing element 16 to respond to concentration changes in gas stream 12. Correspondingly, the distance between sensing element 16 and membrane 36 can be increased when it is desirable to reduce the heat transfer from membrane 36 to sensing element 16.

To provide maximum conductive heat transfer between sensing element 16 and heat pipe 26, sensing element 16 is in solid thermal contact with heat transfer surface 24. Preferably, sensing element 16 is attached to heat transfer surface 24 with a thermally conductive adhesive (not shown).

Support tube 44 is preferably thin-walled stainless steel to minimize its thermal conductance in order to suppress heat flow from metal housing 42 to the most proximal disc 46. Additionally, tube 44 encloses a volume 70 in an annular space between the tube wall and heat pipe 26. Volume 70 can be filled with air or another thermally insulative material to suppress heat flow from tube 44 onto heat pipe 26.

Those skilled in the art will recognize from the foregoing description that the selective gas sensor of the invention can be utilized in a wide variety of applications. For example, sensing element 16 can be configured for the detection of CO and metal wall 54 can be a furnace exhaust gas duct. Alternatively, sensing element 16 can be configured to detect $SO_2$ or another gas pollutant commonly found in industrial emissions.

Thus it is apparent that there has been provided, in accordance with the invention, a selective gas sensor which fully meets the advantages set forth above. Although the invention has been described and illustrated with reference to specific illustrative embodiments thereof, it is not intended that the invention be limited to those illustrative embodiments. Those skilled in the art will recognize that variations and modifications can be made without departing from the spirit of the invention. For example, porous, insulative materials can be included to further regulate heat transfer within the gas sensor. Further, porous materials can fill the passages to further regulate gas flow through the sensor. In addition, different types of attachments exist for mounting the gas sensor to the metal wall, such as clips, brackets, and the like. Still further, additional air spaces can be provided with the sensor housing to further suppress undesirable heat flow. It is therefore intended to include within the invention all such variations and modifications as fall within the scope of the appended claims and equivalents thereof.

We claim:

1. A selective gas sensor comprising:
   a heat exchanger;
   a mechanical support frame mounted to the heat exchanger;
   a sensing element in thermal contact with the heat exchanger;
   a gas-permeable membrane mounted to the mechanical support frame and positioned over the sensing element, the gas-permeable membrane configured for transporting a measurement gas therethrough, the measurement gas having a characteristic temperature;
   an electrochemical oxygen pump mounted to the mechanical support frame and positioned over the gas-permeable membrane,
   wherein a lower surface of the electrochemical oxygen pump is configured to deliver oxygen to the sensing element, and
   wherein an upper surface of the electrochemical oxygen pump is configured to receive the measurement gas;
   an insulating layer overlying the electrochemical oxygen pump; and
   a heating element overlying the insulating layer,
   wherein the heating element maintains the electrochemical oxygen pump at a first temperature, and
   wherein the heat exchanger maintains the sensing element at a second temperature, and
   wherein the second temperature is less than the characteristic temperature of the measurement gas at steady-state conditions and less than the first temperature; whereby the selective gas sensor is segregated into a plurality of distinct thermal management zones for optimal heat conduction within each zone.

2. The selective gas sensor of claim 1, further comprising
   a cover positioned over the mechanical support frame and cooperating with the mechanical support frame to form a passage for the flow of the measurement gas from an external region inward through a sidewall region of the cover and to the upper surface of the electrochemical oxygen pump and outward through an upper region of the cover returning to the external region.

3. The selective gas sensor of claim 1, wherein the heat exchanger is an elongated heat pipe extending away from the sensing element in a direction opposite the electrochemical oxygen pump.

4. The selective gas sensor of claim 1, wherein the heat exchanger is an active element containing a heat transfer fluid.

5. A selective gas sensor comprising:
   a mechanical support frame having porous wall surfaces for the transport of a measurement gas therethrough;
   a porous, thermally-insulating member spanning the mechanical support frame and defining first and second chambers within the mechanical support frame;

an electrochemical oxygen pump mounted within the first chamber and configured to provide oxygen gas into the first chamber and into the second chamber through the porous insulating member during operation of the selective gas sensor;

a thermally conductive body;

a sensing element positioned within the second chamber and in intimate contact with the thermally conductive body, wherein the thermally conductive body forms a portion of an interior surface of the second chamber, and wherein the sensing element is configured to detect a selected component of the measurement gas entering the second chamber through the porous insulating member;

a porous metal cover overlying the mechanical support frame;

a gas permeable thermal insulator surrounding a lower portion of the mechanical support frame and separating the lower portion of the mechanical support frame from the porous metal cover; and means for attaching the selective gas sensor to a metal wall surface; whereby the selective gas sensor is segregated into a plurality of distinct thermal management zones for optimal heat conduction within each zone.

6. The selective gas sensor of claim 5, wherein the thermally conductive body comprises a heat pipe extending away from the second chamber.

7. The selective gas sensor of claim 6, further comprising a plurality of cooling structures thermally attached to the heat pipe.

8. The selective gas sensor of claim 5, wherein the means for attaching comprises:

a threaded metal housing integral with the cover and surrounding the gas permeable thermal insulator; and a threaded boss inserted into the metal wall surface and engaging the threaded metal housing.

9. The selective gas sensor of claim 5 further comprising:

an heat transfer surface of the thermally conductive body extending away from the first chamber;

a cooling disc orthogonally mounted to the heat transfer surface; and a metal tube surrounding the heat transfer surface and coupled to the porous metal cover at an upper end and to the cooling disc at a lower end.

10. A selective gas sensor comprising:

a mechanical support frame having porous wall surfaces for the transport of a measurement gas therethrough, the measurement gas having a characteristic temperature;

a porous insulating member spanning the mechanical support frame and defining first and second chambers within the mechanical support frame;

an oxygen pump mounted within the first chamber;

a sensing element having a lower surface in intimate contact with a thermally conductive body and an upper surface facing the second chamber, wherein the thermally conductive body functions to maintain an optimal characteristic temperature of the sensing element below the characteristic temperature of the measurement gas; and attachment means for securing the selective gas sensor to a wall surface; whereby the selective gas sensor is segregated into a plurality of distinct thermal management zones for optimal heat conduction within each zone.

11. The selective gas sensor of claim 10 further comprising:

a pump housing mounted within the first chamber and surrounding the oxygen pump, the pump housing and the oxygen pump defining an interior cavity within the pump housing; and a conduit within the pump housing for transporting oxygen from the interior cavity into the second chamber.

12. The selective gas sensor of claim 11 further comprising a heater attached to an upper surface of the pump housing and opposite the oxygen pump from the interior cavity.

13. A selective gas sensor comprising:

a mechanical support frame cooperating with a thermally conductive body to define a cavity and configured for conveying a measurement gas into the cavity, the measurement gas having a characteristic temperature;

a sensing element mounted to the thermally conductive body and facing the cavity; and a gas-permeable, thermally-insulating member spanning the mechanical support frame in spaced relationship with the sensing element and controlling a measurement gas flux to the sensing element, wherein the thermally conductive body is configured for transporting heat away from the cavity and cooperates with the gas-permeable, thermally-insulating member to maintain an optimal characteristic temperature of the sensing element below the characteristic temperature of the measurement gas; whereby the selective gas sensor is segregated into a plurality of distinct thermal management zones for optimal heat conduction within each zone.

14. The selective gas sensor of claim 13 further comprising:

a cylindrical cover having a perforated section enclosing the mechanical support frame; and a thermal insulator surrounding a lower portion of the mechanical support frame and separating the cylindrical cover from lower portion of the mechanical support frame.

15. The selective gas sensor of claim 13 further comprising:

an oxygen pump;

a pump support structure mounted within the cavity and cooperating with the oxygen pump to define an oxygen storage chamber, the pump support structure having a conduit for diffusing oxygen from the oxygen storage chamber to the sensing element; and a heater mounted to the pump support structure and overlying the oxygen pump.

16. The selective gas sensor of claim 13, wherein the thermally conductive body comprises:

a heat pipe extending away from the cavity and having a plurality of axially oriented ceramic rods traversing therethrough, wherein each ceramic rod conveys electrical leads coupled to the sensing element.

17. The selective gas sensor of claim 13, wherein the thermally conductive body comprises an active heat exchanger extending away from the cavity.

* * * * *